(12) United States Patent
Fankhauser et al.

(10) Patent No.: US 9,463,547 B2
(45) Date of Patent: Oct. 11, 2016

(54) TOOL CHUCKING DEVICE

(75) Inventors: Marcel Fankhauser, Bern (CH); Bruno Luescher, Zofingen (CH)

(73) Assignee: Robert Bosch GmbH, Stuttgart (DE)

( * ) Notice: Subject to any disclaimer, the term of this patent is extended or adjusted under 35 U.S.C. 154(b) by 377 days.

(21) Appl. No.: 13/981,524

(22) PCT Filed: Dec. 27, 2011

(86) PCT No.: PCT/EP2011/074107
§ 371 (c)(1),
(2), (4) Date: Nov. 9, 2013

(87) PCT Pub. No.: WO2012/100894
PCT Pub. Date: Aug. 2, 2012

(65) Prior Publication Data
US 2014/0070499 A1  Mar. 13, 2014

(30) Foreign Application Priority Data
Jan. 25, 2011   (DE) ......................... 10 2011 003 100

(51) Int. Cl.
| | |
|---|---|
| *B24B 45/00* | (2006.01) |
| *B24B 23/04* | (2006.01) |
| *B24B 23/02* | (2006.01) |
| *B27B 5/32* | (2006.01) |

(Continued)

(52) U.S. Cl.
CPC .............. B24B 23/04 (2013.01); *A61B 17/148* (2013.01); *B24B 23/022* (2013.01); *B24B 23/046* (2013.01); *B24B 45/00* (2013.01); *B24B 45/003* (2013.01); *B24B 45/006* (2013.01); *B27B 5/32* (2013.01); *B27B 19/006* (2013.01); *Y10T 279/33* (2015.01)

(58) Field of Classification Search
CPC ... B24B 45/006; B24B 45/00; B24B 45/003; B24B 23/022; B24B 23/04; B24B 23/046; B27B 5/32; B27B 19/006; Y10T 279/33; A61B 17/148
See application file for complete search history.

(56) References Cited

U.S. PATENT DOCUMENTS 4,597,227 A * 7/1986 Gentischer et al. .......... 451/342
5,058,909 A * 10/1991 Rudolf et al. .................. 279/8
5,157,873 A * 10/1992 Rudolf et al. ............... 451/342

(Continued)

FOREIGN PATENT DOCUMENTS

CN  101497191 A   8/2009
CN     1902029 B   8/2011

(Continued)

OTHER PUBLICATIONS

International Search Report corresponding to PCT Application No. PCT/EP2011/074107, mailed Apr. 23, 2012 (German and English language document) (5 pages).

*Primary Examiner* — Eric A Gates
*Assistant Examiner* — Paul M Janeski
(74) *Attorney, Agent, or Firm* — Maginot, Moore & Beck LLP

(57) ABSTRACT

A tool chucking device, especially an oscillation tool chucking device, includes at least one chucking unit which has at least one chucking element for clamping a treatment tool in an axial direction and at least one control unit for actuating the chucking element. The tool chucking device further includes at least one conversion unit which is designed to modify a conversion ratio depending on at least one movement component of a control element of the control unit.

13 Claims, 4 Drawing Sheets

(51) Int. Cl.
    *A61B 17/14*     (2006.01)
    *B27B 19/00*     (2006.01)

(56) References Cited

U.S. PATENT DOCUMENTS

| | | | |
|---|---|---|---|
| 5,601,483 A * | 2/1997 | Rudolf et al. | 451/359 |
| 6,569,001 B2 * | 5/2003 | Rudolf et al. | 451/344 |
| 7,128,641 B1 | 10/2006 | Lin | |
| 2002/0035882 A1 * | 3/2002 | Hartmann | 74/107 |
| 2003/0190877 A1 * | 10/2003 | Gallagher et al. | 451/344 |
| 2008/0305727 A1 * | 12/2008 | Liersch | 451/359 |
| 2010/0197208 A1 * | 8/2010 | Blickle et al. | 451/342 |
| 2011/0039482 A1 * | 2/2011 | Timmons | 451/344 |
| 2014/0327215 A1 * | 11/2014 | Thorson et al. | 279/141 |

FOREIGN PATENT DOCUMENTS

| | | |
|---|---|---|
| DE | 20 2008 001 759 U1 | 7/2009 |
| EP | 1 180 416 A2 | 2/2002 |
| JP | 6-320409 A | 11/1994 |

\* cited by examiner

TOOL CHUCKING DEVICE

This application is a 35 U.S.C. §371 National Stage Application of PCT/EP2011/074107, filed on Dec. 27, 2011, which claims the benefit of priority to Serial No. DE 10 2011 003 100.6, filed on Jan. 25, 2011 in Germany, the disclosures of which are incorporated herein by reference in their entirety.

BACKGROUND

Tool clamping fixtures, in particular oscillation tool clamping fixtures, which have a clamping unit are already known. The clamping unit here has a clamping element for clamping a machining tool in an axial direction and a control unit for actuating the clamping element.

SUMMARY

The disclosure is based on a tool clamping fixture, in particular an oscillation tool clamping fixture, having at least one clamping unit, which has at least one clamping element for clamping a machining tool in an axial direction and at least one control unit for actuating the clamping element.

It is proposed that the tool clamping fixture comprises at least one conversion unit, which is provided to alter a conversion ratio in dependence on at least one motional component of a control element of the control unit. In this context, the term "provided" is intended to define specially equipped and/or specially designed. By a "clamping unit" should here be understood, in particular, a unit which secures a machining tool by means of a form closure and/or by means of a force closure along the axial direction, in particular to a tool holder of a portable machine tool. Preferably, in a clamping mode of the clamping unit, a clamping force acts along the axial direction on the machining tool.

The clamping element of the clamping unit is preferably of pin-shaped configuration. By a "pin-shaped clamping element" should here be understood, in particular, a clamping element which, in a mounted state, has along the axial direction a longitudinal extent which is greater than a transverse extent of the clamping element along a direction running perpendicular to the axial direction. In particular, the longitudinal extent is more than twice as large as the transverse extent of the clamping element, preferably more than four times as large, and particularly preferably more than six times as large. Preferably, the pin-shaped clamping element is at least partially configured as a hollow body. Particularly preferably, the clamping element has at least two sections, which are configured as legs and are arranged spaced apart at least partially along a direction running at least substantially perpendicular to the axial direction. Preferably, the clamping element is captively disposed in a hollow shaft of the portable machine tool. Particularly preferably, the clamping unit has a clamping chuck disposed on the clamping element. The clamping chuck here preferably comprises two sections, which are movable relative to each other. The sections of the clamping chuck are preferably configured respectively in one piece with one of the legs of the clamping element. By a "clamping chuck" should here be understood, in particular, an element which has at least one clamping surface, which, for clamping of the machining tool, bears in the axial direction at least against a part-surface of the machining tool and applies a clamping force to the machining tool along the axial direction. The term "axial direction" is here intended to define, in particular, a direction which runs preferably at least substantially parallel to a pivot axis and/or rotation axis of a drive shaft and/or spindle of a portable machine tool, which drive shaft and/or spindle is/are provided to drive the machining tool. By "substantially parallel" should here be understood, in particular, an alignment of a direction relative to a reference direction, in particular in one plane, wherein the direction has in relation to the reference direction a deviation of, in particular, less than 8°, advantageously less than 5°, and particularly advantageously less than 2°.

By a "control unit" should here be understood, in particular, a unit which has at least one control element, that can be actuated directly by an operator, and which is provided to influence and/or alter, by an actuating action and/or by the inputting of parameters, a process and/or a state of a unit coupled to the control unit. The term "conversion unit" is here intended to define, in particular, a unit which is provided to convert at least one value of a physical variable, such as, for example, a rotation speed, a torque, a force, etc., into another value of the same physical variable, wherein the two values are in a defined ratio, in particular in a constructively defined ratio, to each other. The conversion unit is preferably formed by a mechanical conversion unit. It is also conceivable, however, for the conversion unit to be designed differently in a manner which appears sensible to a person skilled in the art.

By a "motional component" should here be understood, in particular, a component of a motion variable which mathematically defines a motion, such as, for example, a displacement, a velocity, an angle, etc. Preferably, the motional component is formed by an angle, in particular an opening angle, which the control element of the control unit, in a motion starting from an initial position, traverses. The term "initial position" is here intended to define, in particular, a position of the control element in which a force effect of the control element on the conversion unit and/or the clamping unit for actuation of the clamping unit is lifted and/or prevented. Preferably, a conversion ratio between a path covered by the control element, in particular about a rotation axis running at least substantially parallel to the axial direction, and a path covered by the clamping element along the axial direction is changed by the conversion unit in dependence on an opening angle traversed by the control element. The term "conversion ratio" is here intended to define, in particular, a ratio of physical values which can be changed by means of the conversion unit relative to each other, wherein both physical values differ from zero, in particular the ratio itself likewise differs from a value of zero and/or infinity. By means of the inventive design of the tool clamping fixture, a motional conversion for the actuation of the clamping unit can be influenced. A conversion ratio adapted to a particular application can also advantageously be attained. Good ease of operation can thus be achieved particularly advantageously.

It is additionally proposed that the conversion unit comprises at least one control cam, which, viewed along a course of the control cam at at least two different points on the control cam, has mutually differing pitches in the axial direction. Particularly preferably, the different pitches of the control cam have at the two different points along a course of the control cam in each case a value different from zero.

By a "control cam" should here be understood, in particular, a geometric shape which is provided to convert one motional form into another motional form and/or which is provided to activate, as a consequence of a motion, in particular a motion of the control cam about an axis, a component which as a consequence of the motion executes a motion predetermined by the geometric shape. Preferably, the control cam is provided to convert a rotary motion into a translatory motion. The term "pitch" is here intended to define, in particular, a measure of a steepness of the control cam, in particular viewed in a plane and/or a projection plane. Preferably, the pitch is formed by a mathematically defined pitch, which can be determined by means of a differential quotient and/or by means of a differential equation at any chosen point on the control cam. Preferably, the control cam is disposed on the clamping element on a side of the clamping element which is facing toward the control unit. Particularly preferably, the control cam is configured in one piece with the clamping element. By means of the control cam, a motional conversion can be realized in a constructively simple manner. In addition, by means of the varying pitch of the control cam, a motional conversion adapted to a particular application can be attained. Furthermore, an actuating force to be applied by an operator, for the actuation of the clamping element, can particularly advantageously be influenced by means of the control unit, in particular a course of the actuating force, viewed during an actuation, can advantageously be altered in dependence on an opening angle of the control element.

Advantageously, the conversion unit has at least one scanning element, which is provided to move the clamping element in dependence on the course of the control cam along the axial direction. By a "scanning element" should here be understood, in particular, an element which scans, in particular mechanically scans, the control cam and, as a consequence of the course of the control cam, activates a component, which executes a motion dependent on the course of the control cam. Preferably, the scanning element, at least in an operating state, rests on the control cam. A motion of the clamping element, which motion is dependent on the course of the control cam, can advantageously be attained.

Advantageously, the scanning element is configured as a bolt. By a bolt should here be understood, in particular, an element which has a longitudinal extent greater than a transverse extent running perpendicular to the longitudinal extent. Preferably, the bolt is of cylindrical configuration. Particularly preferably, the bolt is configured rotationally symmetrically about at least one axis. Preferably, the bolt is formed of a solid material. It is also conceivable, however, for the scanning element to have a different design which appears sensible to a person skilled in the art. A scanning element can be attained in a constructively simple manner.

It is further proposed that the bolt has a longitudinal extent which, in a mounted state, runs along a direction extending at least substantially perpendicular to the axial direction. It is also conceivable, however, for the bolt to have a longitudinal extent which, in a mounted state, for the scanning of the control cam, runs along a different direction which appears sensible to a person skilled in the art. A bearing surface and/or a contact surface between the bolt and the control can be attained in a constructively simple manner.

In addition, it is proposed that the tool clamping fixture comprises at least one decoupling unit, which is provided to decouple the control unit, in at least one operating mode, from a motion of the clamping element. By a "decoupling unit" should here be understood, in particular, a unit which has at least one mechanism and/or at least one component which effects a decoupling, in particular a decoupling from motions between at least two elements. Preferably, the decoupling unit is provided to decouple the control unit, in at least one operating mode, from an oscillating motion of the clamping element about a pivot axis of the clamping element, which pivot axis runs at least substantially parallel to the axial direction. A protection of components in at least one operating mode can advantageously be achieved. A long service life of the tool clamping fixture can thus advantageously be attained.

Preferably, the decoupling unit has at least one stop element, which is provided to limit a motion of the clamping element along the axial direction in the direction of the control unit. The stop element, as a consequence of the limitation of the motion of the clamping element along the axial direction, is preferably provided to ensure, at least in one operating state, a distance between the scanning element and the control cam along a direction running perpendicular to the axial direction. A transmission of a motion of the clamping element via the control cam and via the scanning element, in at least one operating state, to the control element of the control unit can thus be prevented.

In addition, it is proposed that the control element of the control unit is configured as a control lever, which is mounted pivotably about a pivot axis running parallel to the axial direction. Preferably, the control lever is mounted pivotably and/or rotatably in a machine tool housing of the portable machine tool. Preferably, the control lever is configured as a one-sided lever, in which actuating forces are transmitted on one side of the control lever. It is also conceivable, however, for the control lever to be designed differently in a manner which appears sensible to a person skilled in the art. An actuating force of an operator for actuation of the clamping element can advantageously be applied by means of the control lever.

Advantageously, the control unit comprises at least one scanner receiving element for receiving a scanning element of the control unit, which scanner receiving element is connected at least in a rotationally fixed manner to the control lever. By "connected in a rotationally fixed manner" should here be understood, in particular, a connection which invariably transmits a torque and/or a rotary motion. Preferably, the scanner receiving element is connected by means of a screw connection in a rotationally fixed manner to the control lever. It is also conceivable, however, for the scanner receiving element to be connected to the control lever by means of a different type of connection which appears sensible to a person skilled in the art, such as, for example, integrally and/or positively. Preferably, the scanner receiving element has at least one recess, in which the scanning element is disposed in a mounted state. A support mounting of the scanning element can advantageously be achieved. In addition, the scanning element, as a consequence of the motion of the control lever, can scan the course of the control cam in a constructively simple manner and thus move the clamping element along the axial direction.

The disclosure is further based on a portable machine tool, in particular a portable machine tool having an oscillatingly drivable spindle, having at least one inventive tool clamping fixture. By a "portable machine tool" should here be understood, in particular, a machine tool, in particular a hand-operated machine tool, which can be transported without a transport machine by an operator. The portable machine tool has, in particular, a weight which is less than 40 kg, preferably less than 10 kg, and particularly preferably less than 5 kg. Good ease of operation for an operator of the machine tool can advantageously be achieved.

The inventive tool clamping fixture is here not intended to be limited to the above-described application and embodiment. In particular, the inventive tool clamping fixture, in order to effect a working method described herein, can have a number of individual elements, components and units which differs from a number stated herein.

BRIEF DESCRIPTION OF THE DRAWINGS

Further advantages emerge from the following drawing description. In the drawing, an illustrative embodiment of the disclosure is represented. The drawing, the description and the claims contain numerous features in combination. The person skilled in the art will expediently also view the features individually and combine them into sensible further combinations, wherein:

DETAILED DESCRIPTION

Figure 1:
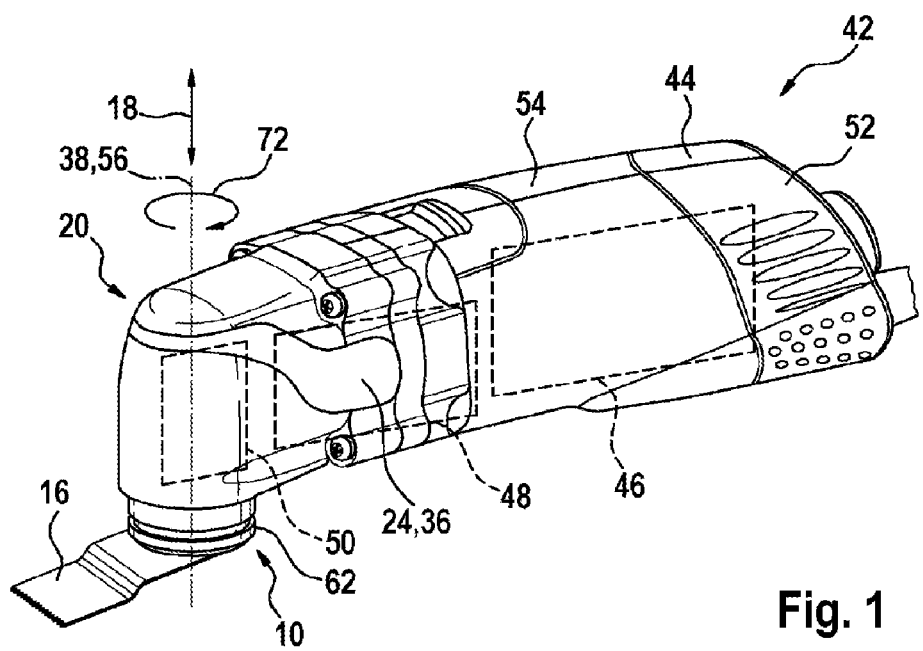
FIG. 1 shows an inventive machine tool having an inventive tool clamping fixture in a schematic representation.
Figure 2:
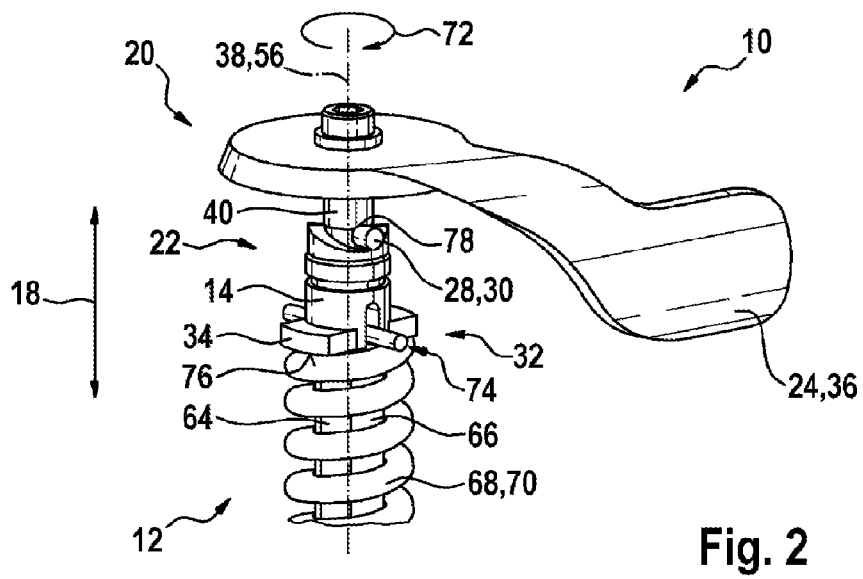
FIG. 2 shows a detailed view of a conversion unit of the inventive tool clamping fixture in a schematic representation.

FIG. 1 shows an electrically operated portable machine tool 42 having a tool clamping fixture 10. The portable machine tool 42 comprises a machine tool housing 44, which encloses an electric motor unit 46, a gearbox unit 48 and a power take-off unit 50 of the portable machine tool 42. The machine tool housing 44 here comprises two housing half shells 52, 54, which are detachably connected to each other along a plane running through an axial direction 18. It is also conceivable, however, for the machine tool housing 44 to have two or more cup-shaped housing parts, which can be detachably connected to each other. The axial direction 18 runs along and/or parallel to a rotation axis 56 of a hollow shaft 60 of the power take-off unit 50, which hollow shaft is configured as a spindle 58 (FIG. 2). The hollow shaft 60 is provided to oscillatingly drive, in a mounted state, a machining tool 16. An oscillating drive of the machining tool 16 is here effected in a manner which is already known to a person skilled in the art, such as, for example, by means of a journal (not represented in detail here) of the gearbox unit 48, which journal is disposed eccentrically on a drive shaft of the electric motor unit 46 and, by means of a link and a vibrating sleeve (not represented in detail here) of the gearbox unit 48, drives the hollow shaft 60 during operation of the portable machine tool 42. The hollow shaft 60 configured as a spindle 58 can thus be driven oscillatingly. For the metal cutting of workpieces, the machining tool 16 can be fastened to a tool holder 62 of the power take-off unit 50. The tool holder 62 is connected in a rotationally fixed manner to the hollow shaft 60 by means of a positive and/or non-positive connection. It is also conceivable, however, for the tool holder 62 to be configured in one piece with the hollow shaft 60. A pivot motion of the hollow shaft 60 can be transmitted to the tool holder 62.

FIG. 2 shows a detailed view of the tool clamping fixture 10. The tool clamping fixture 10 comprises a clamping unit 12, which has a clamping element 14 for clamping the machining tool 16 in the axial direction 18 and a control unit 20 for actuating the clamping unit 14. The clamping unit 14 is of pin-shaped configuration. In addition, the clamping element 14 is arranged movably in the hollow shaft 60. The clamping element 14 here extends along the axial direction 18 through the hollow shaft 60. The clamping element 14 is thus disposed, in a mounted state, in the hollow shaft 60. Furthermore, the clamping element 14 has two legs 64, 66, which, in a mounted state of the clamping element 14, extend at least substantially along the axial direction 18. The legs 64, 66 are configured in one piece with the clamping element 14. The legs 64, 66 also have a small material thickness, viewed along a direction running perpendicular to the axial direction 18, to enable a deflection of the legs 64, 66. As a consequence of material properties and/or a geometric shape of the legs 64, 66, the legs 64, 66 are thus disposed on the clamping element 14 such that they are movable relative to each other. The legs 64, 66 are here arranged resiliently on the clamping element 14. In addition, the legs 64, 66 are arranged spaced apart along the direction running perpendicular to the axial direction 18. As a consequence of the resilient arrangement on the clamping element 14 and the relative distance apart, the legs 64, 66 can move relative to each other along the direction running perpendicular to the axial direction 18.

Figure 5:
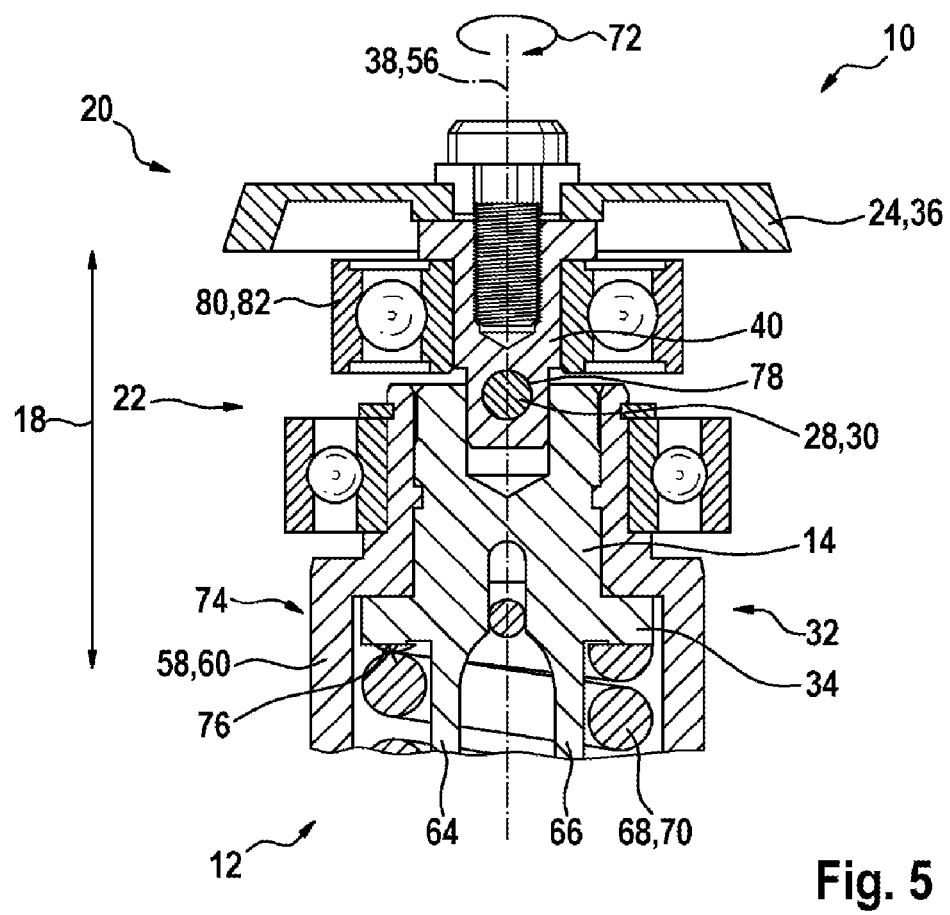
FIG. 5 shows a further sectional view of the inventive tool clamping fixture in a schematic representation.

In addition, the clamping unit 12 has a spring element 68, which is provided to apply a spring force to the clamping element 14 along the axial direction 18 (FIG. 5). The spring element 68 is here configured as a compression spring 70. It is also conceivable, however, for the spring element 68 to be formed by a different spring element which appears sensible to a person skilled in the art, such as, for example, a tension spring, a cup spring, etc. It is likewise also conceivable for the clamping unit 12 to have more than one spring element 68 for applying a spring force to the clamping element 14. The clamping element 14 extends, in a mounted state, along the axial direction 18 through the compression spring 70. The compression spring 70 is thus disposed along a peripheral direction 72 at least around a section of the clamping element 14. The peripheral direction 72 runs in a plane at least substantially perpendicular to the axial direction 18. The compression spring 70 is supported, in a mounted state, with one end 74 against a contact surface 76 of the clamping element 14. The contact surface 76 is here of annular configuration.

Figure 3:
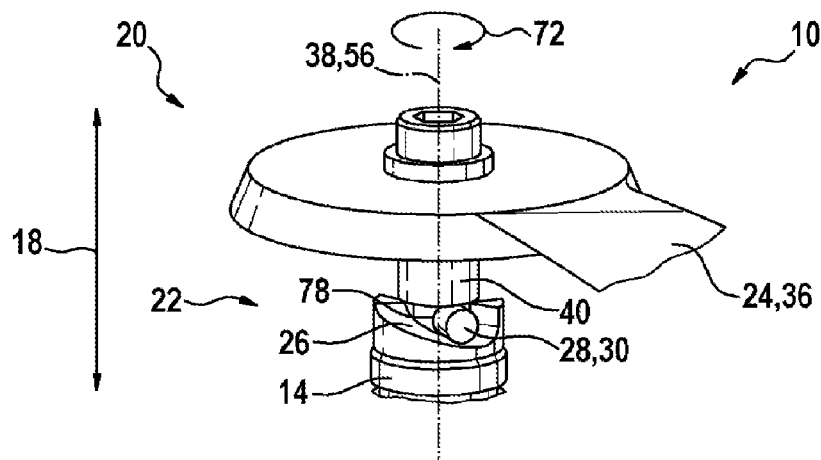
FIG. 3 shows a detailed view of a control cam of the conversion unit of the inventive tool clamping fixture in a schematic representation.

The tool clamping fixture 10 further comprises a conversion unit 22, which is provided to alter a conversion ratio in dependence on at least on one motional component of a control element 24 of the control unit 20. The control element 24 of the control unit 20 is configured as a control lever 36, which is mounted pivotably about a pivot axis 38 running parallel to the axial direction 18. The pivot axis 38 here runs coaxially to the rotation axis 56 of the hollow shaft 60. In addition, the conversion unit 22 comprises a control cam 26, which, viewed along a course of the control cam 26 at at least two different points on the control cam 26, has mutually different pitches in the axial direction 18 (FIG. 3). The control cam 26 is disposed on a side of the clamping element 14 which is facing toward the control unit 20. The control cam 26 is here configured in one piece with the clamping element 14. The conversion unit 22 also has a further control cam (not represented in detail here), which is arranged offset to the control cam 26 along the peripheral direction 72 on the clamping element 14. The further control cam here has a course analogous to the control cam 26. Viewed along a course of the further control cam at at least two different points on the further control cam, the further control cam thus has mutually different pitches in the axial direction 18.

Figure 4:
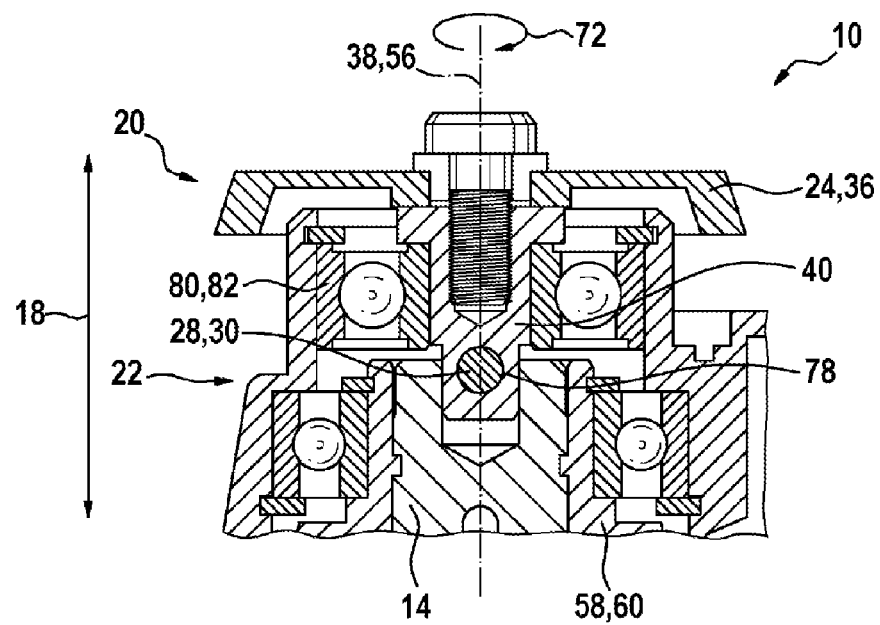
FIG. 4 shows a sectional view of the inventive tool clamping fixture in a schematic representation.

The conversion unit 22 further has a scanning element 28, which is provided to move the clamping element 14 in dependence on the course of the control cam 26 along the axial direction 18. The scanning element 28 is configured as a bolt 30. The bolt 30 has a longitudinal extent which runs, in a mounted state, along a direction extending at least substantially perpendicular to the axial direction 18. In at least one operating mode, the bolt 30 is provided to be brought into contact with the control cam 26 and the further control cam, respectively with two opposite ends of the bolt 30. The control unit 20 comprises a scanner receiving element 40 for receiving the scanning element 28 of the control unit 20, which scanner receiving element is connected in a rotationally fixed manner to the control lever 36. The scanner receiving element 40 extends, in a mounted state, along the axial direction 18. The scanner receiving element 40 further has a recess 78, which extends through the scanner receiving element 40 along a direction running at least substantially perpendicular to the axial direction 18. The recess 78 is formed by a through bore, in which the scanning element 28, in a mounted state, is disposed. A diameter of the recess 78 here corresponds at least substantially to a dimension of the scanning element 28 along the axial direction 18. The scanning element 28 is thus held in the recess 78 by means of a press fit. It is also conceivable, however, for the scanning element 28 to be held differently in the recess 78 in a manner which appears sensible to a person skilled in the art. It is also conceivable, however, for the scanning element 28 to be configured in one piece with the scanner receiving element 40 and to extend away from the scanner receiving element 40 at at least two locations along a direction running at least substantially perpendicular to the axial direction 18. The scanner receiving element 40 is also provided to fulfill a bearing function of the control lever 36 in the machine tool housing 44 (FIG. 4). A bearing element 82 configured as a ball bearing 80 is here disposed on the scanner receiving element 40. The ball bearing 80 encloses the scanner receiving element 40 in a section of the scanner receiving element 40 along the peripheral direction 72.

The tool clamping fixture 10 further has a decoupling element 32, which is provided to decouple the control unit 20 in at least one operating mode from a motion of the clamping element 14. The decoupling unit 32 is provided to decouple the control unit 20, in at least one operating mode, from an oscillating motion of the clamping element 14 about the rotation axis 56. The decoupling unit 32 here has a stop element 34, which is provided to limit a motion of the clamping element 14 along the axial direction 18 in the direction of the control unit 20. In an operating mode, the stop element 34 here bears along the axial direction 18 against a projection of the hollow shaft 60. The control cam 26 disposed on the clamping element 14, and the further control cam, are thus, in an operating mode, arranged distanced from the scanning element 28 along the axial direction 18.

For the mounting of the machining tool 16 on the tool holder 62, the control lever 36, starting from a position of the control lever 36 which bears against the machine tool housing 44, is moved by the operator in a direction pointing away from the machine tool housing 44 and is thus rotated about the pivot axis 38. The scanning element 28 is hereupon moved firstly in the direction of the control cam 26 and of the further control cam until ends of the scanning element 28 configured as a bolt 30 come into contact with the control cam 26 and the further control cam. Upon a further rotary motion of the control lever 36 about the pivot axis 38, the scanning element 28 configured as a bolt 30 slides along the control cam 26 and the further control cam. The clamping element 14 is hereby moved along the axial direction 18 in the direction of the tool holder 62. The clamping unit 12 is hereupon shifted into a tool changing mode. The motion of the clamping element 14 along the axial direction 18 in the direction of the tool holder 62 is here dependent on a course of the control cam 26 and of the further control cam and on an opening angle of the control lever 36. In a motion of the control lever 36 about the pivot axis 38, starting from that position of the control lever 36 which bears against machine tool housing 44, the opening angle is traversed by the control lever 36.

Figure 6:
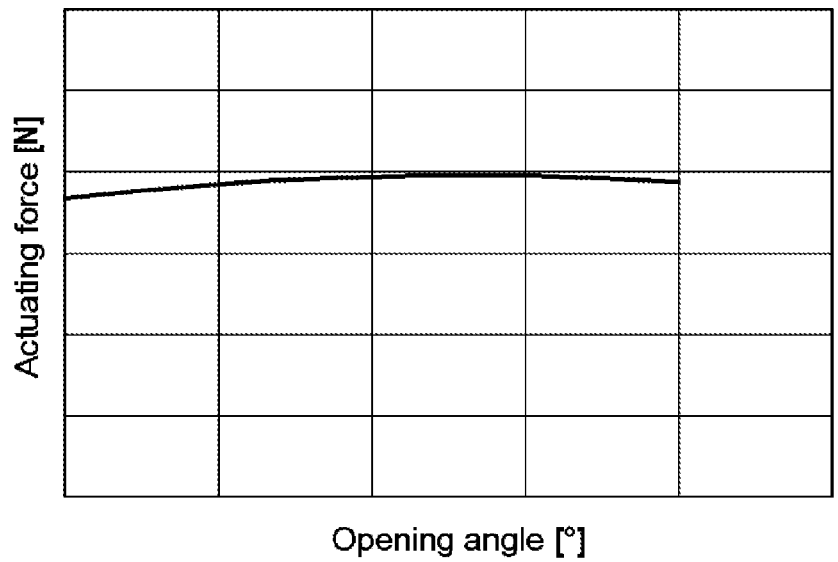
FIG. 6 shows a graph of a course of an actuating force of a control unit of the inventive tool clamping fixture in a schematic representation.

FIG. 6 shows in a graph a relationship between the opening angle traversed by the control lever 36 and an actuating force, to be applied by an operator, for moving the clamping element 14 along the axial direction 18. The graph shows an unproportional course of the actuating force to the opening angle as a consequence of the course and/or a geometry of the control cam 26 and of the further control cam. An actuating force, to be applied by the operator, for moving the clamping element 14 along the axial direction 18 as a consequence of the course and/or geometry of the control cam 26 and of the further control cam is thus also unproportional to the opening angle of the control lever 36.

Figure 7:
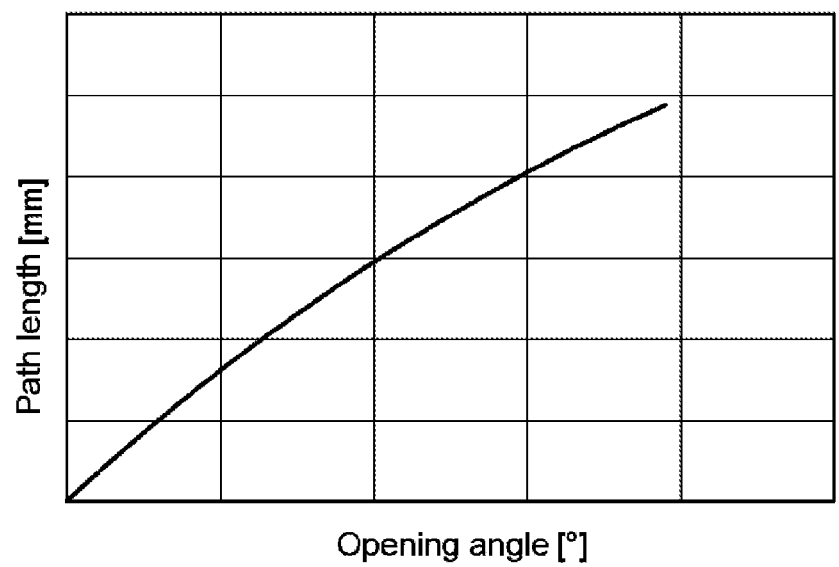
FIG. 7 shows a graph of a course of a motional path of a clamping element of a clamping unit of the inventive tool clamping fixture in a schematic representation.

FIG. 7 shows in a further graph a relationship between a path covered by the clamping element 14 along the axial direction 18 and the opening angle traversed by the control lever 36. As a consequence of the course of the control cam 26 and of the further control cam, a course of the distance is unproportional to the opening angle. The further graph shows an unproportional course of the path length to the opening angle as a consequence of the course and/or geometry of the control cam 26 and of the further control cam. A path of the clamping element 14 which, upon an actuation of the clamping element 14, is covered by means of the control unit 20 along the axial direction 18 as a consequence of the course and/or geometry of the control cam 26 and of the further control cam is thus also unproportional to the opening angle of the control lever 36.

The invention claimed is:

1. A tool clamping fixture, comprising:
  at least one clamping unit having (i) at least one clamping element configured to clamp a machining tool in an axial direction and (ii) at least one control unit configured to actuate the at least one clamping element; and
  at least one conversion unit operatively connected to the at least one clamping element and the at least one control unit, and configured to alter a conversion ratio in dependence on movement of a control element of the at least one control unit, the at least one conversion unit including a control cam surface including a first cam surface portion defining a first cam pitch and a second cam surface portion defining a second cam pitch,
  wherein the first cam pitch is different from the second cam pitch,
  wherein the conversion ratio is a ratio of a change in position of the control element to a change in position of the at least one clamping element, and
  wherein the control element of the at least one control unit is configured as a control lever mounted pivotably about a pivot axis running parallel to the axial direction.

2. The tool clamping fixture as claimed in claim 1, wherein the conversion unit has at least one scanning element configured to move the clamping element in dependence on the course of the control cam along the axial direction.

3. The tool clamping fixture as claimed in claim 2, wherein the scanning element is configured as a bolt.

4. The tool clamping fixture as claimed in claim 3, wherein the bolt has a longitudinal extent which, in a mounted state, runs along a direction extending at least substantially perpendicular to the axial direction.

5. The tool clamping fixture as claimed in claim 1, further comprising at least one decoupling element configured to decouple the control unit in at least one operating mode from a motion of the clamping element.

6. The tool clamping fixture as claimed in claim 1, wherein the control unit comprises at least one scanner receiving element configured to receive a scanning element of the conversion unit, the scanner receiving element being connected at least in a rotationally fixed manner to the control lever.

7. The tool clamping fixture as claimed in claim 1, wherein the tool clamping fixture is an oscillation tool clamping fixture.

8. The portable machine tool as claimed in claim 1, wherein the decoupling unit has at least one stop element configured to limit a motion of the clamping element along the axial direction in the direction of the control unit.

9. The portable machine tool as claimed in claim 1, wherein the first cam pitch and the second cam pitch are mutually differing with respect to a surface of the at least one conversion unit.

10. The portable machine tool as claimed in claim 1, wherein the control element extends from a portion of the at least one conversion unit and is movable relative to the at least one clamping element.

11. A tool clamping fixture, comprising:
at least one clamping unit having (i) at least one clamping element configured to clamp a machining tool in an axial direction and (ii) at least one control unit configured to actuate the clamping element;
at least one conversion unit operatively connected to the at least one clamping unit and the at least one control unit, and configured to alter a conversion ratio in dependence on movement of a control element of the control unit; and
at least one decoupling element configured to decouple the control unit in at least one operating mode from a motion of the clamping element,
wherein the decoupling unit has at least one stop element configured to limit a motion of the clamping element along the axial direction in the direction of the control unit, and
wherein the conversion ratio is a ratio of a change in position of the control element to a change in position of the clamping element.

12. A portable machine tool, comprising:
at least one tool clamping fixture including:
at least one clamping unit having (i) at least one clamping element configured to clamp a machining tool in an axial direction and (ii) at least one control unit configured to actuate the at least one clamping element; and
at least one conversion unit operatively connected to the at least one clamping element and the at least one control unit, and configured to alter a conversion ratio in dependence on movement of a control element of the at least one control unit, the at least one conversion unit including a control cam surface including a first cam surface portion defining a first cam pitch and a second cam surface portion defining a second cam pitch,
wherein the first cam pitch is different from the second cam pitch,
wherein the conversion ratio is a ratio of a change in position of the control element to a change in position of the at least one clamping element, and
wherein the control element of the at least one control unit is configured as a control lever mounted pivotably about a pivot axis running parallel to the axial direction.

13. The portable machine tool as claimed in claim 12, wherein the portable machine has an oscillatingly drivable spindle.

* * * * *